United States Patent [19]

Lübbers et al.

[11] 4,241,738

[45] Dec. 30, 1980

[54] SPECTRAL PHOTOMETER FOR MEDICAL USE IN DETERMINING SKIN COLORATION

[75] Inventors: Dietrich W. Lübbers, Dortmund; Ernst Guilino, Munich, both of Fed. Rep. of Germany

[73] Assignee: Max Planck Gesellschaft zur Förderung der Wissenschaften, Göttingen, Fed. Rep. of Germany

[21] Appl. No.: 895,123

[22] Filed: Apr. 10, 1978

[30] Foreign Application Priority Data

Jun. 13, 1977 [DE] Fed. Rep. of Germany ....... 2726606

[51] Int. Cl.$^3$ .............................................. A61B 5/02
[52] U.S. Cl. ..................................... 128/666; 356/40; 356/418; 356/419
[58] Field of Search .............................. 128/2 A, 2 L; 356/39–41, 308, 326, 418, 419; 128/665–667, 632, 633, 636, 637

[56] References Cited

U.S. PATENT DOCUMENTS

| 2,240,722 | 5/1941 | Snow | 356/308 |
|---|---|---|---|
| 3,460,892 | 8/1969 | Dolin | 356/308 |
| 3,700,331 | 10/1972 | White | 356/308 |
| 3,740,155 | 6/1973 | Keller et al. | 356/418 |
| 3,825,342 | 7/1974 | Lubbers et al. | 356/41 |
| 3,869,212 | 3/1975 | Burcher et al. | 356/308 |
| 4,003,707 | 1/1977 | Lübbers et al. | 128/633 X |
| 4,029,085 | 6/1977 | DeWitt et al. | 128/633 |
| 4,029,419 | 6/1977 | Schumann, Jr. et al. | 356/419 X |
| 4,050,450 | 9/1977 | Polanyi et al. | 128/2 L |
| 4,125,329 | 11/1978 | French et al. | 356/418 X |
| 4,146,332 | 3/1979 | Moore | 356/308 |

FOREIGN PATENT DOCUMENTS 2514478  10/1975  Fed. Rep. of Germany .......... 128/2 L Primary Examiner—Robert W. Michell
Assistant Examiner—Jeffrey W. Tayon
Attorney, Agent, or Firm—Michael J. Striker

[57] ABSTRACT

A housing contains a light source, a monochromator, a photosensitive unit and an oscilloscope-type display. A flexible bundle of fiber-optic elements extends from within the housing out, and is provided at its outer end with a spacing ring. The spacing ring is placed against a skin surface, holding the ends of the fiber-optical bundle properly spaced and oriented relative to the skin surface. At the other end of the bundle, the bundle is subdivided into one branch which receives light from the source, and another branch which emits light reflected from the skin surface into the monochromator. The monochromator projects the spectrum of the skin-reflected light onto the photosensitive unit. The output signal of the photosensitive unit, in a sequential and periodic manner, contains information concerning successive spectral components of the skin-reflected light. The sweep of the display is synchronized with this periodic sequence, so as to display a spectral analysis of the skin-reflected light.

2 Claims, 2 Drawing Figures

SPECTRAL PHOTOMETER FOR MEDICAL USE IN DETERMINING SKIN COLORATION

BACKGROUND OF THE INVENTION

The present invention relates to spectral photometers, of the type comprising a light source, means for receiving light transmitted from the light source and reflected from the object of interest and including a monochromator, as well as means for measuring the received light.

In medicine, diagnostic significance has always been attached to the appearance of the skin, especially the relationship between the coloration of the skin and the flow of blood through skin tissue. However, the color of the skin, in so far as its dependence upon the flow of blood through skin tissue is concerned, depends upon a combination of factors, such as perfusion, the amount and composition of the blood in the capillaries of skin tissue, and the color of the blood hemoglobin, i.e., the degree of oxygenation of the hemoglobin. Accordingly, the actual significance of the coloration of the skin, i.e., for diagnostic purposes, can be quite ambiguous.

In view of this, it would be desirable to be able to separate, at least to some degree, the effects upon the overall appearance of the skin respectively attributable to the various parameters in question. Of course, not only the appearance and coloration of skin, but of other organ surfaces as well, is of interest. With such an object in mind, one possibility would be to evaluate the coloration of the skin with the help of a spectrometer. However, such devices are not only quite expensive but also unwieldy.

Of the factors influencing the appearance and coloration of skin, the single most important one is the conversion of hemoglobin from oxygenated to desoxygenated state (explained for example in Lübbers, Niesel, Pflügers Achiv, "Kurzzeit Spektral Analysator," volume 268, page 286 (1956).

SUMMARY OF THE INVENTION

It is a general object of the invention to simplify the design and operation of known spectral photometers to such an extent, and to so suit them to the application in question, that what results is a diagonostic tool of actual practical utility.

According to one concept of the invention, this can be achieved as follows. A single light conductive (e.g., fiber-optic) structure is utilized for the transmission of light from a light source to the object of interest (e.g., the surface of the skin) and also for the transmission of the light reflected from the object of interest to a monochromator. The monochromator forms a complete spectrum of the received reflected light, and this complete spectrum is projected onto an array of photosensitive elements. The signals produced by the individual photosensitive elements of the array are read out sequentially and cyclically and are displayed on, for example, an oscilloscope. Because each photosensitive element is receiving light of a different part of the spectrum, the oscilloscope display presents a spectral analysis of the coloration of the object of interest, e.g., skin.

One advantage of the invention is that the use of a single light-conducting structure, e.g., a bundle of fiber-optic elements, makes possible the provision of a small, readily manipulated diagnostic probe which can be easily used in the operating room, which can be quickly moved over the surface of the skin or of another organ, and which can be readily sterilized so that it can for example be laid upon and/or moved over the surface of an internal organ exposed during an operation. Furthermore, the spectral resolution of the light containing the information concerning the appearance of the skin, due to the quickness of response of an oscilloscope or the like, suffices to create a display which can be visually evaluated by a diagnostician, who thereby gains a quick overview if the functionally or pathologically determined state of blood flow through the skin tissue. Not to be underestimated is the fact that this makes possible a noninvasive evaluation of the state of blood flow through skin tissue.

According to an advantageous concept of the invention, the end of the light-conducting structure which is to be brought into proximity with the skin (or another organ) is provided with a spacing ring. This brings about an advantage which is of rather great importance in practice and for usefulness of such a diagnostic instrument. Specifically, the spacing ring establishes in a very simple way the correct distance from and relative orientation to the skin for the light-emitting and light-receiving parts of the end of the light-conducting structure. Correct spacing and relative orientation is extremely important, and is a prerequisite for even the possibility of meaningful evaluation. With such a spacing ring, the diagnostician can easily maintain the probe in the exactly correct position and orientation, with hardly any attention or mental concentration being required of him. Likewise, he can quickly move the probe from one location on the skin to another, without having to worry about considerations of proper orientation and spacing.

The spacing ring can additionally be used to contain means operative for performing other measurements upon the skin and/or for positively performing some treatment or other operation upon the skin. For example, when measuring perfusion using the Hensel method, the probe can accommodate a heat-generating element. Or a source of radiation could be provided in the probe for hyperemization. Or the probe could contain means for measuring skin conductivity.

According to a further concept of the invention, use is made of a second light-conducting structure. One end of the second light-conducting structure both emits light onto a reflection standard or reference surface and also receives the light reflected therefrom. The received light is emitted, at the other end of the second light-conducting structure, into the monochromator. The transmission of light into the monochromator from the first and second light-conducting structures is alternative and selectable, and can be used for purposes of calibration and initial setting-up.

In particular, this latter expedient makes possible the establishment of a null line or null curve for display on the oscilloscope screen, so as to be able to take into account and compensate in advance for factors such as changes in the output of the light source employed, changes in the operating characteristics of the electronics of the measuring circuitry, and so forth.

In particular, when one switches over to the second light-conducting structure and the reflection standard, one can equalize the spectral response of the photosensitive elements in the photosensitive-element array, for example by adjusting their individual amplifiers or other associated circuit components. Preferably, this adjustment of the individual photosensitive-element stages is performed by electronic means, in view of the number of photosensitive elements preferably employed.

Preferably, the scanning of the photosensitive-element array is repeated with a frequency in excess of 20 Hz. In this way, the display on the oscilloscope screen can quickly follow motions of the probe across the surface of the skin, so that the amount of interpretable information generated will be limited only by the diagnostician's ability to interpret the display (e.g., depending upon what he is looking for on the display) and the speed with which he wishes to move the probe across the surface of the skin.

If the spectral photometer is to be permitted to include moving parts, then it becomes possible, as one result, to easily avoid the need for a whole array of photosensitive elements. Instead, use can be made of a single photosensitive element positioned to receive light through a cyclically moving monochromator, i.e., a monochromator which progressively transmits onto the photosensitive element successive spectral components of the light reflected from the skin area of interest. The periodic motion of the monochromator can be used to synchronize, for example, the x-direction sweep of the oscilloscope, whereas the output signal from the photosensitive element feeds the y-direction deflection of the oscilloscope.

With this latter expedient, it is particularly advantageous that the periodically moving monochromator be provided in the form of a rotating filter, the angularly successive portions of which transmit successive spectral components.

According to a further concept of the invention, use is again made of a second light-conducting structure, but in a different way than mentioned above. A single first photosensitive element is used as just described, i.e., in conjunction with a periodically moving monochromator, and a second photosensitive element is additionally provided. The second light-conducting structure transmits light from the light source of the instrument directly through the periodically moving monochromator, and onto the second photosensitive element. The output signals derived from the two photosensitive elements are applied to the input of a divider, and the output signal of the latter is used to drive the display.

This formation of a quotient tends to greatly reduce the effect of the light-emitting characteristics of the source upon the ultimate displayed information. For example, if the lamp used for the light source is replaced, it will not be necessary to recalibrate the equipment.

When the periodically moving monochromator is a rotating filter of the type just mentioned, then it is particularly advantageous that the relationship of transmitted wavelength and angular position of the rotating filter be sinusoidal.

Such filter can be produced relatively easily using vapor deposition techniques, and would be typically provided together with a block filter for harmonics-suppression on a circular carrier plate. When this carrier plate then rotates, during a single rotation there is performed both a forward and reverse runthrough of the spectrum. The oscilloscope is advantageously set up for this fact, so that its return sweep is not performed as a flyback but instead at the same sweep speed as its forward sweep. This results in the formation of two spectral displays on the oscilloscope screen, per rotation of the filter.

The expense for the display unit can be reduced by using, instead of a precision oscilloscope, a television picture tube. This is feasible, because the speed at which the measuring operation in question is performed is slow enough to be implemented with the magnetic deflectors of a picture tube.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

DESCRIPTION OF THE PREFERRED EMBODIMENTS

Figure 1:
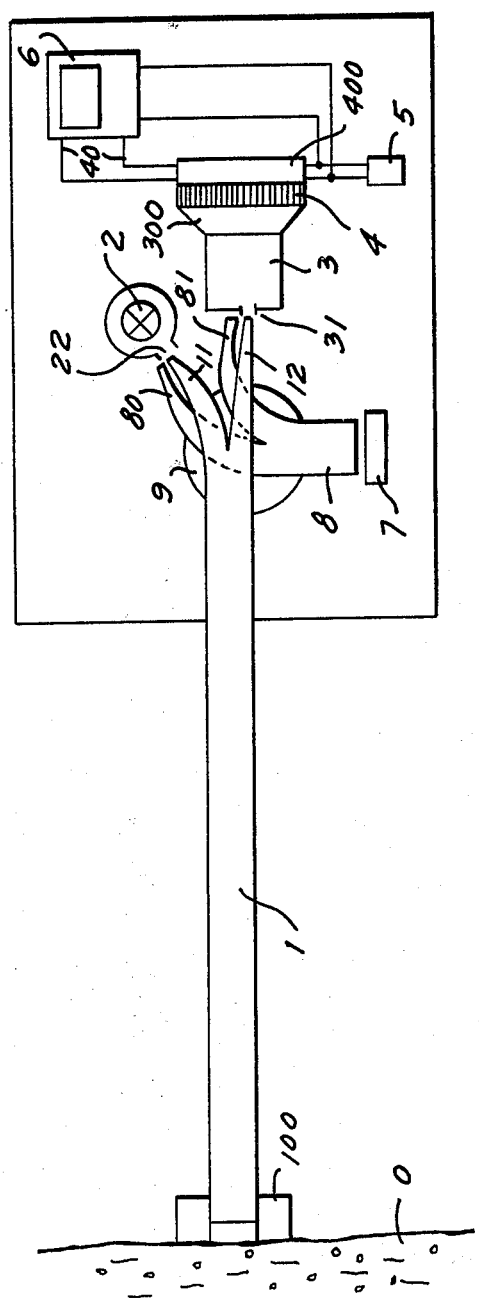
FIG. 1 depicts a first embodiment of the invention.

A light-conducting structure 1 is oriented toward an object O of interest, e.g., the surface of the skin of a patient. The light-conducting structure 1 is here comprised of a bundle of fiber-optic elements. At the object end (left end) of the structure 1, the light-conducting elements which emit light onto the object, and those which receive the reflected light, are interspersed among one another. At their other ends, the fiber-optic elements are subdivided into two groups 11 and 12. Group 11 receives light from the light source 2. Group 12 emits light, which has been altered with respect to spectral composition as a result of reflection from the object O, into the input slit 31 of a monochromator 3. The monochromator 3 resolves the received light into a spectrum 300 which is focussed onto a light-measuring unit 4, comprised of several hundred successive photocells arranged in a straight row. Each photocell may, for example, be provided with a separate amplifier of its own. In any event, the output signal of each photocell is applied to one input of a respective gate, the other input of which receives an enablement signal when the signal from that photocell is to be transmitted. The transmission of signals from successive photocells is controlled by a synchronizer 5, for example a ring couunter whose successive outputs are each connected to a successive input of the succession of gates associated with the photocells. The outputs of the gates of the photocells are all connected to the signal input 40 of an oscilloscope 6, e.g., to control the y-direction deflection thereof. The synchronizer 5 additionally controls the x-direction sweep of the oscilloscope; either the synchronizer triggers the x-direction sweep, or else it actually controls each increment of x-direction sweep. During operation, there accordingly appears on the oscilloscope screen a spectral display of the light reflected from the object O. The frequency at which the photocell row is scanned is preferably greater than 20 Hz. This makes for a persisting image and, at the same time, a quick change of the display, e.g., if the diagnostician shifts the probe to another area of the skin.

To calibrate the equipment, for example to take into account the spectral composition of the light emitted by light source 2 or the differing sensitivities of the photocells in the photocell row, the left end of light-conducting structure 1 can be placed against a reflection standard, i.e., a surface whose color serves as a standard for calibration. If an across-the-board flat null line is desired, the reflection standard can be merely a layer of material which equally reflects light of all wavelengths of interest. However, another expedient is also contemplated. The embodiment of FIG. 1 includes a second light-conducting structure 8 which, along with the first such structure 1, is mounted on a rotatable plate 9. The right end of second light-conducting structure 8 is subdivided into two parts 80 and 81. The lower end of light-conducting structure 8 is permanently positioned to emit light onto a reflection standard 7 and to receive the light reflected therefrom. In the illustrated angular position of rotatable plate 9 (the operating position, not the calibrating position), the light source 2 and light-measuring unit cooperate with the first light-conducting structure 1. If the rotatable plate 9 is turned clockwise a small distance, the end 80 of second light-conducting structure 8 lines up with the output slot 22 of the light source 2, and the end 81 with the input slit 31 of the monochromator 3. When this is done, the null line (properly calibrated or not) appears on the screen of the oscilloscope 6. If the null line does not have the desired shape, then the sensitivity of each photocell in the photocell array can be adjusted, for example by means of an associated potentiometer and amplifier stage, until the null line does have the desired shape.

If the null line is to be a straight line, then one can make use of known electronic calibrating means 400, operative for automatically altering the signal level of each photocell to assume a prescribed value, e.g., by automatically changing the gain of the amplifier stages associated with the respective photocells.

At its left end, the first light-conducting structure 1 is provided with a spacing ring 100, which the diagnostician places against the surface of the skin to be examined. The spacing ring 100 serves to establish, in a very simple way, the correct spacing between the end of the fiber-optic bundle and the skin, and the correct orientation. The spacing ring 100 can accommodate sensors, for example to measure skin temperature, or measuring electrodes, for example to measure skin conductivity, or can also contain means for performing some operation or treatment upon the skin, for example a source of radiation or a heater. In particular, it may be desired to heat the skin in the course of measuring perfusion, i.e., a measurement which would be related to and useful in the interpretation of the spectral display on the oscilloscope screen.

The operation of the embodiment depicted in FIG. 1 does not involve moving parts. If the provision of moving parts is to be permitted, then it becomes possible to very conveniently dispense with the need for the photocell array 4, and to use instead a single photocell. This is shown in the embodiment of FIG. 2.

Figure 2:
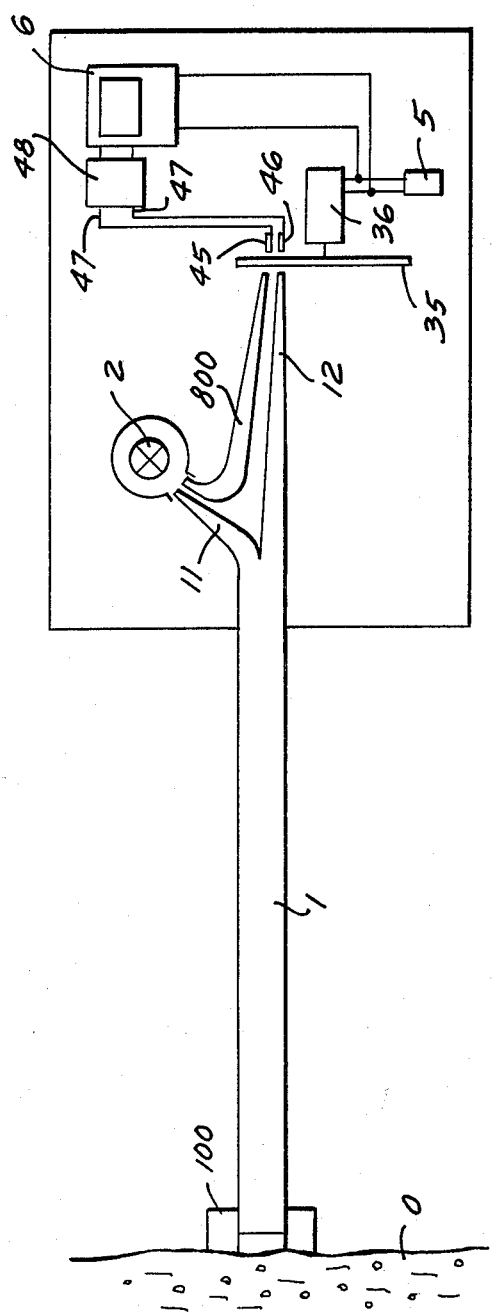
FIG. 2 depicts a second embodiment of the invention.

In FIG. 2, the light-conducting structure 1, spacing ring and other such components are provided as in FIG. 1. The photocell array is replaced by a single photocell 46. The photocell 46 is located behind a monochromator 35, here in the form of a rotatable filter driven by a motor 36. Angularly successive sections of the filter 35 transmit light of successive respective wavelengths. Preferably, the relationship of transmitted wavelength and angular position of the rotary filter is sinusoidal. The motor 36, for example a stepper motor, is here driven by the synchronizer 5 which, here again, also controls the x-direction sweep of the oscilloscope 6. The oscilloscope is preferably set so that its return sweep is performed not as a flyback but instead at the same sweep speed as its forwards sweep. Use can also be made of a synchronizer 5 operative for implementing an x-direction oscilloscope sweep with a sinusoidal time base. The output signal from photocell 46 could be fed directly to the y-deflection signal input of the oscilloscope 6.

However, in the embodiment of FIG. 2, the output of photocell 46 is not directly connected to the signal input of the oscilloscope 6. Instead, there is provided alongside photocell 46 a further photocell 45. A second light-conducting structure 800 receives light emitted from light source 2 and transmits it through the rotating filter 35 onto the second photocell 45. The two photocells 45, 46 are decoupled from each other so that photocell 45 receives only light via light-conducting structure 800, and photocell 46 only light from part 12 of the light-conducting structure 1. The output signals from the photocells 45, 46 are transmitted via signal lines 47 to the input of a divider 48 which produces a corresponding quotient output signal, which is then fed to the y-deflection signal input of the oscilloscope 6. The photocells are so located as to receive light through substantially the same location on the rotating filter 35. Accordingly, the formation and display of a quotient signal renders the displayed spectral analysis, to a very great degree, independent of the light-emission characteristics of the light source 2, e.g., those resulting from aging or lamp replacement, and independent of the transmissivity of the rotating filter 35.

Advantageously, the display 6, instead of being an oscilloscope, can be a less expensive T.V. receiver picture tube. The frequency at which the measurement operation is performed is low enough to be implemented using the magnetic-deflection capabilities of a T.V. receiver, i.e., does not absolutely require the use of an oscilloscope.

It will be understood that each of the elements described above, or two or more together, may also find a useful application in other types of constructions and circuits differing from the types described above.

While the invention has been illustrated and described as embodied in a diagnostic tool for assessing skin coloration, it is not intended too be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A spectral photometer for use in evaluating the coloration of the human skin surface, of the type having a light source, light-conducting means and light-sensitive means for generating signals dependent upon intensity of the light received therein, in the combination comprising: the light conducting means, including flexible fiber optics members interspersed among one another, having one end and a second end: a support and spacing ring, said one end being positioned within said spacing ring to establish the correct spacing between said light-conducting means and the skin surface, said second end being divided into a first branch and into a second branch, said light source being arranged to emit light into said first branch, whereby the light is transmitted through said light-conducting means onto the skin surface, reflected from the latter, transmitted back through said light-conducting means and emitted from said second branch; monochromator means for receiving the light emitted from said second branch and spectrally projecting it onto said light-sensitive means, said monochromator means comprising means operative for projecting onto the light-sensitive means successive portions of the spectrum of the light received from the second branch in a progressive and periodic sequence; display means connected to receive signals generated by the light-sensitive means and produce a spectral display of the light reflected from the skin surface, said display means comprising an oscilloscope having an information-signal input connected to the light-sensitive means, and sychronizing means for synchronizing the sweep of the oscilloscope with the periodic operation of said monochromator means, said monochromator means comprising a rotating filter having angularly successive sections to transmit successive parts of the spectrum of the light received from said second branch onto said light-sensitive means.

2. The spectral photometer of claim 1, further comprising: photo-sensitive means including a first photosensitive element positioned to receive light from said second branch through said rotating filter, and a second photosensitive element, second light-conducting means having a first end positioned to receive light emitted by said light source and a second end positioned to emit light through said rotating filter onto said second photosensitive element, and signal-dividing means having two inputs each connected to receive the signal produced by a respective one of two photosensitive elements and having an output connected to the information-signal output of said oscilloscope.

* * * * *